United States Patent
Al-Khouri

(10) Patent No.: US 11,026,989 B2
(45) Date of Patent: Jun. 8, 2021

(54) **COMPOSITION FOR TREATING ERECTILE DYSFUNCTION BY *ORCHIS ANATOLICA* EXTRACT**

(71) Applicant: Jordan University of Science and Technology, Irbid (JO)

(72) Inventor: Nabil Azar Al-Khouri, Irbid (JO)

(73) Assignee: JORDAN UNIVERSITY OF SCIENCE AND TECHNOLOGY, Irbid (JO)

(*) Notice: Subject to any disclaimer, the term of this patent is extended or adjusted under 35 U.S.C. 154(b) by 41 days.

(21) Appl. No.: 16/597,212

(22) Filed: Oct. 9, 2019

(65) Prior Publication Data

US 2020/0038469 A1 Feb. 6, 2020

Related U.S. Application Data

(62) Division of application No. 15/133,840, filed on Apr. 20, 2016, now Pat. No. 10,441,622.

(51) Int. Cl.
*A61K 36/898* (2006.01)

(52) U.S. Cl.
CPC ...... *A61K 36/898* (2013.01); *A61K 2236/333* (2013.01)

(58) Field of Classification Search
None
See application file for complete search history.

(56) References Cited

PUBLICATIONS

Allouh, M. et al., "Orchis Anatolica Root Ingestion Improves Sexual Motivation and Performance in Male Rats," Journal of Complementary and Integrative Medicine, vol. 7, issue 1, article 39, 2010, 12 pages.

Khouri, N. et al., "Histopathological Effects of Short and Long Term Treatment of Orchis Antolica Crude Root Extract on Female Albino Rats Fertility and Pregnancy," Pakistan Journal of Biological Sciences, vol. 15, No. 4, 2012, pp. 198-202.

Khouri, N. et al., "Effects of orchids (*Orchis anatolica*) on reproductive function and fertility in adult mice," Reproductive Medicine and Biology, vol. 5, pp. 269-276, Jun. 30, 2006.

Khouri, N. et al., "Antidiabetic effect of Orchis anatolica root extracts on alloxan-induced diabetic rats," Comp. Clin. Pathol., vol. 22, pp. 347-354, Jan. 31, 2012.

*Primary Examiner* — Russell G Fiebig
(74) *Attorney, Agent, or Firm* — Matheson Keys & Kordzik PLLC; Kelly Kordzik

(57) ABSTRACT

A composition for treating erectile dysfunction in a male mammal comprising an *Orchis anatolica* root bulb extract. A method of treating erectile dysfunction in a mammal comprises administering a therapeutically effective amount of *Orchis anatolica* root bulbs alcohol extract in a male mammal.

3 Claims, 1 Drawing Sheet

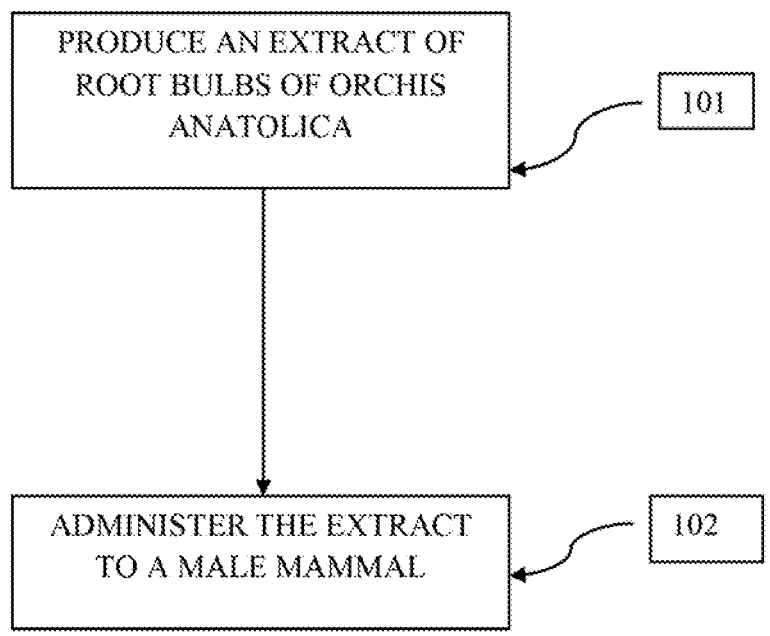

COMPOSITION FOR TREATING ERECTILE DYSFUNCTION BY ORCHIS ANATOLICA EXTRACT

This application is a divisional of U.S. patent application Ser. No. 15/133,840, issued as U.S. Pat. No. 10,441,622 on Oct. 15, 2019.

TECHNICAL FIELD

The present invention relates in general to treatment of erectile dysfunction ("ED"), and more particularly to, treatment of ED in mammals by administrating an effective amount of *Orchis anatolica* root bulbs alcohol extract.

BACKGROUND INFORMATION

Penile erection is a complicated physiological process that involves not only the blood vessel system, but also the endocrine and nervous systems. Patients suffering from erectile dysfunction ("ED") are definitely on the increase by the reasons of the expanded life span, the increase of adult diseases, change of diet, and the increase of industrial and traffic accidents. In addition, the increase of mental stress and physical fatigue resulting from complicated modern life could contribute to aggravate this manifestation.

The methods for the treatment of ED are diversified, ranging from medicinal treatment including male hormones, and injection of vasodilators in the corpus cavernous smooth muscle, to surgical treatments, including vascular surgery, and surgical implantation of a penile prosthesis. Medicinal treatments, such as male hormones, yohimbine, apomorphine, and traszodone, are not suitable for the treatment of a severe form of ED. Such medicines have side effects, and even their effects on treating such manifestation are in doubt. Diversified agents able to relax the corpus cavernous smooth muscle have also been used. Such medication includes adrenergic alpha-receptor blockades, cholines, NO (nitric oxide), peptides, prostaglandin, histamines, calcium channel inhibitors, calcium channel openers, nonspecific vasodilators, and more. Although sildenafil has been introduced as a primary treatment for ED, innovation of a specific medicine that can have a reliable reproducibility has not been reported yet.

*Orchis anatolica* Boiss, also known as Anatolian Orchid, belongs to the Orchidaceae family. The *Orchis anatolica* plant occurs in various parts of the eastern Mediterranean region, including mainland Greece, and an area extending from the southern Aegean islands of Turkey to Iran. This plant is found also in diversified and specific locations within the pine forest regions in northern Jordan. Out of this family of plants, several species are considered important and popular for their effect in treating many diseases. In the literature, a study indicated that there is an effect of *Orchis anatolica* root ingestion on the sexual motivation and performance of male rats; however, no tests were carried on the effect of *Orchis anatolica* root bulb alcoholic extract on the treatment of erectile dysfunction in male mammals (see, Allouh et al., "*Orchis anatolica* Root Ingestion Improves Sexual Motivation and Performance in Male Rats," Journal of Complementary and Integrative Medicine, Vol. 7, Iss. 1, Article 39, 2010). Thus, there are no previous reports in the literature emphasizing the effect of *Orchis anatolica* on ED.

SUMMARY

In accordance with embodiments of the present disclosure, an ethanol extract of *Orchis anatolica* root bulbs induced the penile erection in male rodents and rabbits. Embodiments of the present disclosure also confirmed that such extract can be effectively used for the production of a treatment agent to overcome ED, ranging from mild to severe cases.

Embodiments of the present disclosure provide a method of treating ED in a male mammal comprising administrating an *Orchis anatolica* root bulbs alcohol extract to a mammal in need thereof.

In embodiments of the present disclosure, the alcohol may be chosen from methanol, ethanol, propanol, or butanol.

In embodiments of the present disclosure, the alcohol is 70% ethanol.

Embodiments of the present disclosure provide a method of relaxing corpus cavernous smooth muscles in a male mammal comprising administrating a *Orchis anatolica* root bulbs alcohol extract to a mammal in need thereof.

In embodiments of the present disclosure, the alcohol is chosen from methanol, ethanol, propanol, or butanol.

In embodiments of the present disclosure, the alcohol is 70% ethanol.

BRIEF DESCRIPTION OF THE DRAWINGS

FIG. 1 illustrates a flow chart of a method for treating erectile dysfunction in a mammal, configured in accordance with embodiments of the present disclosure.

DETAILED DESCRIPTION

Embodiments of the present disclosure provide a treatment of erectile dysfunction in a male mammal, comprising administering a *Orchis anatolica* root bulbs alcohol extract to a male mammal.

Referring to FIG. 1, aspects of the present disclosure comprise a first step 101 of producing an extract of root bulbs of *Orchis anatolica* (e.g., in either a pharmaceutically or nutraceutically acceptable form), as further described herein, and then, in a second step 102, administering a therapeutically effective amount of the extract to a male mammal.

The extract may be produced in a following manner. *Orchis anatolica* plant may be harvested, and then the roots separated and air dried. The dried roots may be ground into powder and then mixed with a liquid (for example, distilled water or alcohol (e.g., methanol, ethanol, propanol, or butanol)) before being administered by oral gavage, or being prepared into an otherwise therapeutically effective amount (for example, in a pharmaceutically or nutraceutically acceptable form) to facilitate its ingestion.

*Orchis anatolica* Boiss belongs to the Orchidaceae family and is also known as Anatolian Orchid. *Orchis anatolica* plants used in embodiments of the present disclosure occur in various parts of the eastern Mediterranean region, including mainland Greece, and an area extending from the southern Aegean islands of Turkey to Iran, and in diversified specific locations within the pine forest regions in northern Jordan. An extract of *Orchis anatolica* of embodiments of the present disclosure are extracted from roots. Herein, the roots mean all the non-aerial underground parts of the plant. The extract may be extracted from root bulbs of *Orchis anatolica*. The root bulbs are the potato shaped tuberous roots.

An extract may be manufactured as an alcohol extract. Such an alcohol extract may be selected from a group consisting of methanol, ethanol, propanol, and butanol. The concentration of alcohol may be 100%, and may preferably be 70%.

From the perspective of histology, a remarkable feature of the male penis is its core of erectile tissue ("ET") columns, each enclosed by its own dense, fibrous connective tissue capsule, named the tunica albuginea. Erectile tissue contains a specialized arrangement of arteries, shunts, and venous sinusoids within a matrix of connective tissue and smooth muscle, forming a highly structured criss-crossing of interconnected fibers and spaces that are tensed as the cylinder expands during an erection. Penile ET contains numerous variably shaped spaces (i.e., vacuoles, vascular spaces) lined with simple squamous epithelium, which are separated from one another by trabeculae containing connective tissue and specially arranged smooth muscle cells. Arterial branches irrigating the corpora cavernosa penetrate the walls of the trabeculae of these ET and form either capillary plexuses, which supply the vascular spaces, or continue as coiled arteries (helical arteries). This vascular arrangement forms an important source of blood supply to the vascular spaces during penile erection. Blood flowing in the deep artery of the penis may flow either into the corpora cavernosa or into an arterio-venous anastomosis, which connects directly with efferent veins, and which is usually dilated. In a flaccid state, almost all the blood from the deep artery passes directly into the dilated arterio-venous shunt. Therefore, minimal amounts of blood pass into the corpora cavernosa. Blood that does enter the corpora divides into two routes: the helicine arteries that empty directly into the blood spaces of the erectile tissue, and the nutritive arteries of the trabeculae, which, after breaking up into a capillary network, re-form into small veins, then empty into the cavernous spaces. Cavernous spaces are drained by veins that pierce the tunica albuginea and constitute the efferent venous return. During an erection, blood flow into the deep artery of the penis increases. Concomitantly, the opening of the arterio-venous anastomosis is reduced by active vasoconstriction, resulting in a slightly dilated artery passing through the tunica albuginea into the cavernous body. The helicine arteries then dilate the cavernous spaces and fill them with blood. Blood flow leaving the cavernous body is not reduced. Herein, the vascular supply to this tissue determines the erectile aspect of the penis, whereas its impairment leads to ED.

An erection, on the other hand, is mediated by parasympathetic impulses that pass from the sacral portion of the spinal cord through the pelvic nerves to the penis. These parasympathetic nerve fibers, in contrast to most other parasympathetic fibers, are believed to release nitric oxide (NO) and/or vaso-active peptide in addition to acetylcholine. Nitric oxide (NO) exhibits a relaxant effect on the penile arteries and the trabecular meshwork of smooth muscle fibers within the penile tissue. Therefore, the inability of the cavernosal smooth muscle to relax in normal condition could be related to either reduction of NO production and/or synthesis or to damage or dysfunction of the corporal tissue, a condition known as ED.

ED is defined as the inability of a male to attain or maintain an erection long enough to complete the sexual act. This condition affects over 50% of men over the age of 50 years. With age, penile tissue becomes dysfunctional following sexual stimulation as a result of an inability of the penile arteries and the corporal smooth muscle cells to relax leading to the development of the ED. Recent data suggest that by the age of 40, about 40% of men may suffer from ED, and this is increased to almost 70% by the end of the sixth decade of life, which could be mainly vasculo-genic in origin. The success of the drug sildenafil (Viagra®) in improving erections in men suffering from ED is due to the fact that this drug is a phosphodiesterase ("PDE") inhibitor that improves the relaxation of the penile arteries and the corpora smooth muscle tissue by augmenting the effect of the NO.

Although considerable advanced research has been made to find an ideal treatment for ED, a well potent treatment for this problem has not been identified. The use of herbal medicine, enriched by information from plant research, has always played a primary role in the treatment of this condition. Herbal medicinal plants with yohimbine and red Korean *Panax Ginseng* are examples of traditional plants treatments for ED, whereas their usage is burdened with serious adverse effects. One of the therapeutic claims for the *Panax ginseng* is that it enhances sexual function in laboratory animals. A study conducted by the Southern Illinois University School of Medicine in 2002 found that both forms of Asian and American *Ginseng* enhance the copulatory performance in male rats and mice. The effect of *Ginseng* could be either due to changes in hormone secretion with emphasis on the elevation of the testosterone serum titer, or as a direct effect of its ginsenoside components on the central nervous system and through a feedback mechanism on the gonadal tissues. Another study indicated that *Panax Ginseng* directly can cause endothelium-dependent vasodilatation and relaxation of rabbit penile corpus cavernosum in vitro enforcing its role in treatment of ED.

When the extract from root bulbs of *Orchis anatolica* was used to treat corpus cavernous smooth muscle in the Example disclosed herein, the relaxation of the smooth muscle thereof increased in a dose-dependently manner.

The extract of *Orchis anatolica* according to embodiments of the present disclosure may be added to food as it is or together with other food or food ingredients, and may be formulated by conventional methods. There is no limitation in food applicable to the extract of embodiments of the present disclosure. A mixing rate for the effective ingredients may be determined as a function of the purpose of use (e.g., prevention, improvement, or treatment).

Embodiments of the present disclosure provide a treating agent for erectile dysfunction containing an alcohol extract of root bulbs of *Orchis anatolica* as an active ingredient. One or more pharmaceutically acceptable carriers can be additionally added to make a pharmaceutical formulation containing the extract. The carrier can be selected from a group consisting of saline, buffered saline, water, glycerol, and ethanol, but the selection is not limited thereto.

The extract according to embodiments of the present disclosure may be administered orally, and may be used in general forms of pharmaceutical formulations. The extract according to embodiments of the present disclosure can be prepared for oral administration by mixing with generally used fillers, extenders, binders, wetting agents, disintegrating agents, diluents such as surfactant, and/or excipients.

The effective dosage of the extract according to embodiments of the present disclosure may be determined according to age, gender, health condition, absorption of an active ingredient, inactivation rate, excretion, and other medicines applied together. Embodiments of the present disclosure may include pharmaceutical formulations in dosage units. This means that the formulations may be present in the form of individual parts, for example tablets, coated tablets, capsules, pills, suppositories, and/or ampoules, the active compound content of which corresponds to a fraction or a multiple of an individual dose.

Solid formulations for oral administration may be in the form of tablets, pills, dusting powders, and capsules. Liquid formulation for oral administrations may be in the form of suspensions, solutions, emulsions, and/or syrups, and the above mentioned formulations may contain various excipients, such as wetting agents, sweeteners, aromatics, and/or preservatives, in addition to generally used simple diluents, such as water and/or liquid paraffin.

Embodiments of the present disclosure will be further described in the following Example without, however, limiting the same thereto.

EXAMPLE

In vitro dose dependent relaxation effect of *Orchis anatolica* root bulbs ethanol extract on penile tissue suspended in physiological bath solution after an induced contraction and compared to Sildenafil and red Korean *Panax ginseng* for the same therapeutic purpose.

Method:

A water-jacketed physiological organ bath provides a stable and adjustable way of organ stability and temperature control. Substrates and other nutrients that are required to sustain tissue function were provided via a physiological solution (e.g., Krebs solution). This will allowed the study of evoked tissue responses to pharmacological agents and/or electrical stimulation.

Tissue Preparation:

Penile tissues from a mature New Zealand rabbit (e.g., 3-3.5 kg) and albino rats (e.g., 300-350 g) were dissected out and cleaned of the outer adherent connective tissue, and the two corpora cavernosa integral tissues were obtained. Each corpus cavernosum was cut lengthwise into 4 pieces measuring about 2 mm thick and 10-12 mm long out of which a 7-8 mm long piece was taken from the middle part of each strip by removing the two unwanted edges of these strips. The strips were kept in a well oxygenated Krebs solution, pre-cooled to 4° C., and placed in a refrigerator until the initiation of the experiment.

Tissue Mounting and Equilibration:

Each erectile tissue ("ET") was mounted by clipping both of its ends within the bath. An ET strip was hooked to one clip end, which was tied to a metal wire (e.g., mounting hook), which was fixed to a bottom of a water-jacketed chamber. The top end of the strip was clipped to a cotton thread and connected to a lever (e.g., arm), which was connected to a Harvard isotonic transducer. The former was connected to a Harvard Universal Oscillograph for recording the force of contraction to an isotonic transducer. The tissue strip was stretched against a fixed caliber weight of 2 gm attached to the lever of the isotonic transducer. The free movable lever end was horizontally adjusted receptive to any movement according to the contraction and relaxation of the ET within the path when stimulated. Before each experiment, the transducer was calibrated two times against this caliber weight. The bath into which the tissue was mounted contained 25 ml of oxygenated Krebs solution with continuous oxygenation (gas mixture of 95% $O_2$ and 5% $CO_2$ and at 37° C.) and left for 60 minutes before starting the experiment.

Extract Preparation:

Certain specifications for collection of *Orchis anatolica* plants were adopted so that the intact roots together with the potato-shaped bulb parts were collected and preserved intact. Bulbs were detached from roots and left to dry at air temperature, and then separated into two categories: a large rounded sized bulb resembling the small sized potato (male bulb) and an elongated small sized bulb (female or feeding bulb). The round potato shaped bulb was chopped and grinded using an electrical grinder until a powder was obtained. Each 500 g of dried and grinded *orchis* roots was then refluxed in (2 L) 70% ethanol at 50° C. for 36 hours in a continuous extraction (soxhlet) apparatus. Ethanol extract was filtered and concentrated under reduced pressure at 50° C. using a rotary evaporator. Red Korean *Panax Ginseng* was obtained from a South Korea market as a concentrated powder vacuumed and sealed in metal container packages of 50 g (commercially obtained from KOREAEXPORT CO LTD). Powder was dissolved well in distilled water from which different concentrations were used. Different doses of both *Orchis anatolica* extract and Red Korean *Panax Ginseng* were used to obtain and determine the maximum effect of ET response. A sildenafil concentration of 1 mM was chosen because it is considered to be a supra-maximum dose based on clinical findings that an oral therapeutic dose of 100 mg will rarely result in free plasma concentrations of >40 nM.

Physiological Buffer Solution "Krebs Solution Preparation":

A 1 liter Krebs stock solution was prepared the day before the experiment containing the following chemicals: NaCl (125 mM), $NaHCO_3$ (20 mM), KCl (4 mM), $NaH_2PO_4$ (1.8 mM), $MgSO_4$ (1.8 mM), $CaCl_2$ (1.8 mM), glucose (10 mM), and HEPES buffer (10 mM) (see Table 1). For a final 1 liter Krebs solution, 725 ml ringer and 700 ml Deionized water were added. The solution pH was set to 7.4 after gassing with 95% $O_2$/5% $CO_2$ for 30 minutes before it was used. Krebs solutions were freshly prepared on each experimental day from the stock solutions stored in the refrigerator.

TABLE 1

Krebs Ringer Buffer

| | Gram/Liter | Final Concentration | |
|---|---|---|---|
| NaCl | 8.5 g | 145 mM | |
| KCL | 0.37 g | 5.0 mM | |
| $MgCl_2$ | 0.26 g | 1.3 mM | (omitted for Cell prep) |
| $NaH_2PO_4$ | 0.15 g | 1.2 mM | |
| Glucose | 1.8 g | 10 mM | |
| Hepes | 4.8 g | 20 mM | |

Final pH adjusted to 7.4 with 1 M NaOH

Drug Preparation:

*Orchis anatolica* and Red Korean *Panax Ginseng* selective doses were prepared by adding different concentrations of each treatment directly into the bath chamber containing a 25 ml Krebs solution (a 0.013 g *Orchis anatolica* represents a dose of 400 mg/kg mice body weight in vivo treatment). Each treatment was added, multiplied according to the trial dose needed, together with Phenylephrine into the bath chamber containing a penile strip. To prepare different concentrations of Sildenafil (0.001 g=100 mM or 0.002 g=200 mM), these concentrations were added to the Krebs solution accordingly when different concentrations were needed. These Sildenafil concentrations were chosen as it is considered to be a supra-maximum dose based on clinical findings that an oral therapeutic dose of 100 mg will rarely result in free plasma concentrations of >40 nM.

Phenylephrine ("PE") Preparation:

In penile arteries, materials like noradrenaline ("NA"), phenylephrine ("PE", $\alpha_1$-AR agonist) caused concentration-dependent contractions. A 100 ml Krebs solution containing 0.0509 gm Phenylephrine was added into a 100 volumetric glass flask to make stock solution, which was kept refrigerated until used. 10 ml, 25 ml, and 50 ml of Phenylephrine stock solution were added to 90 ml, 250 ml, and 500 ml Krebs, respectively, to yield a 250 µM concentrated dose.

Measurements of Tissue and Organ Activity "Recordings Parameters":

Penile tissue contraction was induced by adding L-Phenylephrine to a Krebs solution in the bath, which was indicated by a downward movement of the transducer, which was recorded on a chart paper as an upward movement. The distance between the baseline and the highest point on the recorded trace represented the maximum contraction force generated ("MCF"). The relaxation induced by Sildenafil, Orchis anatolica, and/or Red Korean Panax Gensing, moved the lever upwards, representing relaxation of the tissue, which was recorded and traced as a downward movement on the chart. Distance from the maximum point to the lowest point on the trace after the induction of relaxation represented a maximum relaxation force ("MRF") generated in the tissue. During these experiments, the downward tracer recordings represented the state of relaxation, and they were measured at repeated intervals of 5, 10, 15, 20, 25, and 30 minutes. The decrease in the trace was expressed as a percentage of the maximum contraction produced before inducing the relaxation.

Experimental Protocol:

Strips of penile tissues (e.g., 2 mm×2 mm×7 mm) were mounted in water-jacketed chambers (25 ml, Harvard-USA), and heated to 37° C. with continuous oxygenation (95% oxygen and 5% $CO_2$). Strips were equilibrated in a NaCl Krebs solution for 1 hour before proceeding, then this solution was replaced with a high $K^+$ Krebs solution ($K^+$=109 mM/L) placed in the chambers. The isotonic contraction of the strips within the solution was recorded until it reached a constant steady state, which took about 15-20 minutes. The strips were then washed again with a normal Krebs solution for at least two times, and the tissue was allowed to return to a complete relaxation state (in about 30 minutes). The tissue then was contracted replacing the normal Krebs solution with L-Phenylephrine (250 mM). After reaching the peak force of contraction (approximately 5-10 minutes), the solution was replaced with a Krebs solution containing L-Phenylephrine (250 mM) and SNP (300 mM), or both SNP (300 mM) and one of the drugs used in the experiment (Sildenafil, Orchis, and Ginseng), which was added in an appropriate concentration (200-600 mM) to the chamber for the time intervals mentioned above.

Results:

Preliminary results indicated that a dose dependent relaxation of penile tissue was reached when Orchis anatolica was added to the Krebs solution together with phenylephrine. Table 2 indicates results obtained after different treatments that were applied to the bath chamber (containing strips of penile tissues (e.g., 2 mm×2 mm×7 mm) mounted in water-jacketed chambers). These results are expressed in percentage of contraction (−%) or relaxation (+%) of the penile tissue recorded.

TABLE 2

| Treatment | Time dependent penile tissue contraction (−) and relaxation (+) response to treatment | | | | |
| --- | --- | --- | --- | --- | --- |
| | 5 | 10 | 15 | 20 | 25 |
| High $K^+$ Krebs | −3% | −5% | −6% | −6.5% | −6% |
| L-Phenylephrine (0.0509 gm stock solution) | −6.8% | −8.2% | −9.5% | −10% | −10% |
| Orchis anatolica (0.026 mg/50 ml Krebs) | 10% | 16% | 18% | 19% | 20% |
| Orchis anatolica (0.052 mg/50 ml Krebs) | 34% | 36% | 38% | 42% | 42% |
| Panax ginseng (0.052 mg/50 ml Krebs) | 5% | 6% | 7% | 9% | 9% |
| Sildenafil (0.002 g/50 ml Krebs) | 11% | | 12% | | 24% |

SUMMARY

The preliminary results indicated that an Orchis anatolica plant root bulbs extract in a concentration of 0.026 g/50 ml induced up to 16% relaxation of the smooth muscle of the penile cavernosal tissue after 10 minutes exposure. These results were obtained after inducing contraction using phenylephrine into the bath with erectile tissue. An additional 16% relaxation was further noticed in the erectile tissue strips when a higher dose of Orchis anatolica (0.052 g/50 ml) was used after 10 minutes of its application. These measured parameters indicated greater erectile tissue relaxation effects of Orchis anatolica plant when compared with Sildenafil, Red Korean Panax Ginseng, and the controls. These results also indicated that the relaxation of the erectile tissue corpus cavernosum is dose dependent with greater affinity when an Orchis anatolica plant root bulbs extract was used. Thus, an ethanol extraction of an Orchis anatolica root plant can play an important role in improving male erectile function in penile tissue in mammals.

While the present invention has been described in details and with reference to specific embodiments thereof, it will be apparent to one skilled in the art that various additions, omissions, and modifications can be made without departing from the spirit and scope thereof.

The invention claimed is:

1. A formulation for treating erectile dysfunction in a male mammal comprising an effective amount of an Orchis anatolica root bulb extract, wherein the Orchis anatolica root bulb extract was extracted with 70% ethanol as an extraction solvent, and wherein the formulation is in the form selected from the group consisting of tablets, coated tablets, capsules, pills, suppositories, and/or ampoules.

2. The formulation as recited in claim 1, wherein the effective amount of the Orchis anatolica root bulb extract is configured to relax smooth muscle in penile cavernosal tissue.

3. The formulation as recited in claim 1, wherein the effective amount of the Orchis anatolica root bulb extract is configured to relax corpus cavernosum erectile tissue.

* * * * *